United States Patent
Lee et al.

(10) Patent No.: US 10,434,057 B2
(45) Date of Patent: Oct. 8, 2019

(54) COSMETIC COMPOSITION COMPRISING OSMANTHUS ASIATICUS EXTRACT AND CLEMATIS APIIFOLIA EXTRACT

(71) Applicant: AMI COSMETIC CO., LTD., Seoul (KR)

(72) Inventors: Kyung Rok Lee, Seoul (KR); Byung Seok Han, Anyang-si (KR); Kyung Min Kim, Jeju-si (KR); Jeong Hwan Kim, Jeju-si (KR); Su Yeong Kim, Jeju-si (KR); Ji Mi Kang, Jeju-si (KR)

(73) Assignee: AMI COSMETIC CO., LTD., Seoul (KR)

( * ) Notice: Subject to any disclaimer, the term of this patent is extended or adjusted under 35 U.S.C. 154(b) by 0 days.

(21) Appl. No.: 15/837,454

(22) Filed: Dec. 11, 2017

(65) Prior Publication Data

US 2019/0038546 A1    Feb. 7, 2019

(30) Foreign Application Priority Data

Aug. 4, 2017 (KR) ........................ 10-2017-0099037

(51) Int. Cl.
*A61K 8/9789*   (2017.01)
*A61Q 19/02*    (2006.01)
*A61Q 19/08*    (2006.01)

(52) U.S. Cl.
CPC ............ *A61K 8/9789* (2017.08); *A61Q 19/02* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2006/0134095 A1* | 6/2006 | Ito | A61K 8/19 424/125 |
| 2015/0104399 A1* | 4/2015 | Ceccoli | A61K 8/97 424/59 |
| 2015/0209271 A1* | 7/2015 | Faller | A61K 8/347 424/766 |

FOREIGN PATENT DOCUMENTS

| | | | |
|---|---|---|---|
| EP | 0131176 A1 | * | 6/1984 |
| KR | 20040005345 | * | 7/2002 |
| KR | 20140114240 A | * | 9/2014 |

* cited by examiner

*Primary Examiner* — Robert A Wax
*Assistant Examiner* — Danah Al-Awadi
(74) *Attorney, Agent, or Firm* — Novick, Kim & Lee; Jae Youn Kim

(57) ABSTRACT

A cosmetic composition including an *Osmanthus asiaticus* extract and a *Clematis apiifolia* extract as active ingredients is provided.

6 Claims, 1 Drawing Sheet

COSMETIC COMPOSITION COMPRISING OSMANTHUS ASIATICUS EXTRACT AND CLEMATIS APIIFOLIA EXTRACT

CROSS-REFERENCE TO RELATED APPLICATION

This application claims priority to and the benefit of Korean Application No. 10-2017-0099037, filed on Aug. 4, 2017, the disclosure of which is incorporated herein by reference in its entirety.

BACKGROUND

1. Field of the Invention

The present invention relates to a cosmetic composition including an *Osmanthus asiaticus* extract and a *Clematis apiifolia* extract as active ingredients.

2. Discussion of Related Art

The skin is an important organ that protects the body from physical, chemical or biological stimuli. Also, the skin plays an important role in maintaining homeostasis in living bodies, for example, regulating moisture and body temperature in the skin, and the like.

However, the skin undergoes changes due to various internal and external factors with age. When secretion of various hormones regulating metabolism in the skin is reduced, and the function of immunocytes and the activities of skin cells are degraded, various troubles such as inflammation and atopy occur on the skin. Also, free radicals and reactive oxygen species are increasingly generated due to the dysfunction of the skin, and melanin is deposited in cells, thereby causing damage to the skin due to spots, freckles, wrinkles, and the like.

To improve such skin, various cosmetic compositions for external use for the skin have been developed. Particularly, functional cosmetic compositions include an antioxidant for removing free radicals and reactive oxygen species, both of which cause oxidative stress. Generally, the "antioxidant" in the cosmetics has an ability to significantly reduce or prevent a condition in which the function and structure of the skin damaged by oxidation are degraded and destroyed, and serves to restore the skin damaged by exposure to ultraviolet rays.

The cosmetics industry has developed a number of products using natural substances in order to reduce irritation of the skin caused by various chemicals. Because natural materials have few side effects with respect to the skin, the natural materials have an increasing value for development as raw materials for cosmetics with a current increase in consumers' responses to cosmetics using such natural materials. Particularly, medicinal plants have attracted attention as raw materials for cosmetics because the medicinal plants have various functions including an anti-cancer effect.

However, cosmetic products containing a natural substance-derived extract obtained by conventional methods have drawbacks in that the cosmetic products do not sufficiently realize antioxidant, anti-inflammatory, and whitening functionalities, and the skin-improving activity of the cosmetic products does not last consistently. Therefore, a need for development of natural substance-derived cosmetic products having excellent functionality and in vivo stability and a high skin-improving effect has emerged steadily.

*Clematis apiifolia* (*C. apiifolia*) is a medicinal plant that commonly grows on mountains and in fields, and has anti-inflammatory, analgesic, diuretic, and antidiarrheal effects. *C. apiifolia* has a wide range of effects on neuralgia, facial nerve palsy, cerebral apoplexy, migraines, myogenic palsy, rheumatoid arthritis, sore knees, backaches, gout, paralyzed hands and feet, bones stuck in the throat, and the like, and has been used for medicinal purposes against edema caused by nephritis due to an excellent diuretic action thereof. However, no skin-improving activity for development of cosmetics is known so far.

Therefore, under the circumstances in which the need for development of natural substance-derived cosmetic products having excellent functionality and in vivo stability and a high skin-improving effect has emerged steadily, the present inventors have endeavored to develop a cosmetic composition having excellent functionality using *C. apiifolia*.

SUMMARY OF THE INVENTION

Therefore, the present invention is designed to solve the problems of the prior art, and it is an object of the present invention to provide a cosmetic composition having excellent functionality, which includes an *Osmanthus asiaticus* (*O. asiaticus*) extract and a *Clematis apiifolia* (*C. apiifolia*) extract.

According to an aspect of the present invention, there is provided a cosmetic composition including an *O. asiaticus* extract as an active ingredient.

According to one exemplary embodiment, the cosmetic composition may further include a *C. apiifolia* extract.

According to one exemplary embodiment, the cosmetic composition may further include one or more selected from the group consisting of a *Puerariae radix* extract, a *Glycyrrhiza uralensis* Fischer extract, a *Farfarae flos* extract, a *Sophora flavescens* extract, a *Magnolia officinalis* extract, a *Blettia rhizome* extract, a *Rhus semialata* extract, an *Eleutherococcus senticosus* (Rupr. & Maxim.) Maxim. root extract, a *Persiccae Semen* extract, a *Liriope platyphylla* extract, a *Panax ginseng* extract, a *Cnidium officinale* Makino extract, a *Cyperi Rhizoma* extract, a *Morus Alba* bark extract, a *Perilla ocymoides* extract, a *Portulaca oleracea* extract, a *Scutellaria baicalensis* extract, an *Angelicae Gigantis* Radix extract, a *Coptis chinensis* extract, a *Flos Sophora japonica* Linne extract, a *Phellodendron amurensis* extract, a *Polygonum Multiflorum* extract, and a *Houttuynia cordata* thunb. extract.

According to one exemplary embodiment, the cosmetic composition may be used for antioxidant and whitening purposes.

According to one exemplary embodiment, the extract of the cosmetic composition may be extracted with one or more solvents selected from the group consisting of water, an anhydrous or hydrated lower alcohol having 1 to 4 carbon atoms, acetone, ether, ethyl acetate, butyl acetate, trichloromethane, dichloromethane, chloroform, hexane, and 1,3-butylene glycol.

According to one exemplary embodiment, the cosmetic composition may be formulated into one or more selected from the group consisting of an emulsifying toner, a nourishing toner, a moisturizing cream, a nourishing cream, a massage cream, a nourishing lotion, an essence, an ampoule, a gel, an eye cream, an oil, a foundation, a cleansing cream, a cleansing foam, a cleansing water, a shampoo, a rinse, a pack, a spray, and a powder.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Although general terms used as widely as possible are selected as terminology used in the exemplary embodiments in consideration of the functions of the exemplary embodiments, the terms may vary depending on the intention of one of ordinary skill in the art, the judicial precedents, the advent of new technologies, and the like. Terms arbitrarily selected by the applicant may also be used in a specific case. In this case, their meanings can be obtained based on the detailed description of the exemplary embodiments. Accordingly, the terms used in the present invention should be defined based on the meanings of the terms and the contents of the entire specification, and not by simply stating the terms themselves.

Unless otherwise defined in this specification, all the terms used herein, including technical and scientific terms, have the same meanings as what are generally understood by a person skilled in the related art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The numerical ranges include numerical values defined within these ranges. All the maximum numerical limits given throughout this specification include all lower numerical limits although such lower numerical limits are expressly written herein. All the minimum numerical limits given throughout this specification include all higher numerical limits although such higher numerical limits are expressly written herein. All the numerical ranges given throughout this specification include all narrower numerical ranges that fall within such broader numerical ranges although such narrower numerical ranges are expressly written herein.

Hereinafter, exemplary embodiments of the present invention will be described in detail. However, it will be apparent that the following embodiments are not intended to limit the scope of the present invention.

According to one aspect of the present invention, there is provided a cosmetic composition including an *Osmanthus asiaticus* (*O. asiaticus*) extract and a *Clematis apiifolia* (*C. apiifolia*) extract as active ingredients.

Because the cosmetic composition includes a natural substance-derived extract as the active ingredient, the cosmetic composition has a high skin-improving effect and excellent in vivo safety, and skin irritation may also be minimized.

The expression "including/comprising as an active ingredient" may mean that the active ingredient is included at an effective amount that may express a skin-improving effect, for example, an effective amount that may synthesize collagen associated with an anti-wrinkle effect, an elasticity-improving or skin-whitening effect, an effect of relieving skin irritation, a skin soothing effect, and the like.

"*Osmanthus asiaticus*" is an evergreen broad-leaved shrub of the family Oleaceae. The leaves are opposite each other, lancet-shaped (somewhat oblong or oval in shape), and serrated or flat at the edge. The leaves are 7 to 12 cm in length and 2.5 to 4 cm in width, and have recessed veins and embossed veins at the rear. The flowers are dioecious and off-white in color, grow at the axil, and have a very good fragrance. The calyx and petal are divided into four parts, and has two stamens and one stigma. The fruit is a round stone fruit, and ripens to deep purple in May of the following year when the flowers blossom. The plant is native to China and grows mainly in southern regions of Korea.

"*C. apiifolia*" is a plant vine of the family Ranunculaceae of the order Ranunculales. The plant commonly grows on mountains and in fields and is approximately 3 m in length. Young leaves and stalks are edible, and the plant is distributed in Korea, Japan, and China. *C. apiifolia* has anti-inflammatory, analgesic, diuretic, and antidiarrheal effects, and the roots are referred to as *Clematis florida* Thunb., and has a medicinal effect on lumbago and cerebral apoplexy. The stalk is referred to as *C. apiifolia* A.P. DC and used to treat fever, edema, diarrhea, and the like.

The cosmetic composition may further include one or more selected from the group consisting of a *Puerariae radix* extract, a *Glycyrrhiza uralensis* Fischer extract, a *Farfarae flos* extract, a *Sophora flavescens* extract, a *Magnolia officinalis* extract, a *Blettia rhizome* extract, a *Rhus semialata* extract, an *Eleutherococcus senticosus* (Rupr. & Maxim.) Maxim. root extract, a *Persiccae Semen* extract, a *Liriope platyphylla* extract, a *Panax ginseng* extract, a *Cnidium officinale* Makino extract, a *Cyperi Rhizoma* extract, a *Morus Alba* bark extract, a *Perilla ocymoides* extract, a *Portulaca oleracea* extract, a *Scutellaria baicalensis* extract, an *Angelicae Gigantis* Radix extract, a *Coptis chinensis* extract, a *Flos Sophora japonica* Linne extract, a *Phellodendron amurensis* extract, a *Polygonum Multiflorum* extract, and a *Houttuynia cordata* thunb. extract.

"*Puerariae radix*" is a root of *Puerarialobata Ohwi* from which the periderm is removed, according to the Korean Pharmacopoeia, and has been widely used among ordinary people in favorite foods, drinks, health foods, and the like. In oriental medicine, *Puerariae radix* is used to relieve a condition such as body aches from cold, eruptive diseases, neck pain, and the like because it serves to loosen knotted muscles, help an increase in energy in the spleen and stomach to make an essence to quench thirst, and has an antidiarrheal effect.

"*Glycyrrhiza uralensis* Fischer" is a plant referred to as 'Gukro,' 'Micho,' 'Milgam,' 'Milcho,' 'Yeongtong,' and 'Cheomcho.' The husk of *Glycyrrhiza uralensis* Fischer is reddish or dark brown in color and has wrinkles in a longitudinal direction. Sometimes, the husk has lenticels, eye buds and scaly leaves grown thereon, give off a particular smell, and tastes sweet. In oriental medicine, *Glycyrrhiza uralensis* Fischer is known to harmonize toxicities of all drugs to allow the drugs to take effect, control chills, fevers, and bad energy in the metacarpus, dilate all blood vessels, and strengthen muscles and bones.

"*Farfarae flos*" is a perennial flower that belongs to the family Chrysanthemum. In oriental medicine, the flower is characterized by suppressing a cough and discharging phlegm because the flower has an effect of moistening the lungs. Particularly, the flower is known to be effective for a cough caused by a pulmonary collapse, bloody phlegm, pulmonary tuberculosis, and pulmonary abscess. Also, the flower has been widely applied to coughs, asthma, and upper respiratory infections caused by exogenous pathogenic factors, and release stagnated energy to form a uniform skin "*Sophora flavescens*" is a perennial grass of the family Leguminoceae of the order Rosales belonging to the dicotyledon group, and is referred to as a 'thief's cane,' 'Neosam,' and 'snake's shade tree.' The root of *Sophora flavescens* from which the periderm is peeled off is known as a raw material having an antiseptic effect as well as an effect of suppressing fungal growth in the skin, a skin moisturizing effect, a whitening effect, and an effect of improving blood circulation. *Sophora flavescens* is effective for jaundice, dysentery, leukorrhea, and genital pruritus caused by lower energizing dampness and heat, an affected area is washed with water boiled with the root in the case of the pruritus. Also, the root is used to treat skin pruritus, pustules, scabies or psoriasis, and is known to be effective for hypouresis or painful symptoms caused by heat accumulation.

"*Magnolia officinalis*" is an evergreen broad-leaved tree of the family Lauraceae of the order Ranunculales belonging to the dicotyledon group, and grows in Korea, Japan, Taiwan, and southern China. Since ancient times, the bark of the stalks and branches has been used for medicinal purposes to treat asthma and gastrointestinal disorders, and contains components such as magnolol, isomagnolol, honokiol, machiol, and the like. Among these, honokiol has been used as a useful material which belongs to the polyphenol class and has antidepressant, antithrombotic, nerve-tranquilizing, and antibacterial effects.

"*Blettia rhizome*" is a tuber of grown *Bletilla striata* Reichb. fil., and a fresh raw tuberous root contains 14.6% water, 30.48% starch, and 1.5% glucose, and also contains essential oils and mucilage. The root contains *bletilla* mannan. *Blettia rhizome* is known to have a good local hemostatic action, a hemostatic action in which blood cells are coagulated to cause artificial thrombosis, have an antibacterial effect, and may be used to treat pulmonary tuberculosis, silicosis and complications of pulmonary tuberculosis.

"*Rhus semialata*" is a gall formed when *Schlechtendalia chinensis* of the family Aphididae of the order Hemiptera parasitizes leaves of *Rhus chinensis* of the family Anacardiaceae, has uneven shapes, for example, a saccular or broken shape irregularly divided into 2 to 4 pieces. The outer surface is grayish brown in color, covered with light brown short hair, hard and easily broken. The gall is hollow, but contains light gray starch or dead bugs and secretions. *Rhus semialata* has been used to treat chronic and persistent coughs, chronic diarrhea, rectal prolapse, cold sweats, ganacratia, and the like, all of which are caused by weak lungs due to strong astriction and treat rectal bleeding, nose bleeding, uterine bleeding, traumatic bleeding, vomiting, dermatitis, and pruritus. The gall has pharmacological actions such as an astringent effect, an antibacterial action, a hepatoprotective action, an antioxidant action, and the like.

"*Eleutherococcus senticosus* (Rupr. & Maxim.) Maxim." grows naturally in regions such as Odaesan, Jirisan, and the like, and also grows in Manchuria, Siberia, Hokkaido, and the like. The plant is known to exert a promoter action to enhance the entire function of living organs and strengthen environmental adaptation and defensive power of the living organs.

"*Persiccae Semen*" is a mature seed of a peach tree that belongs to the family Rosaceae, contains fatty oils (40 to 50%), amygdalin, triolein, and water-soluble proteins PR-A and PR-B (Shigeru et al., Shoyakugaku Zasshi 40, 2, 129, 1986), and is known to treat anticoagulated blood and discharge phlegm, exert an intestine lubricating action and treat stagnant blood.

"*Liriope platyphylla*" is a perennial plant that reproduces by rhizomes and seeds, and is generally distributed on low hills at the height of 500 m or less in Korea, and the leaves are evergreen throughout the year (Huh, M. K., H. W. Huh, J. S. Choi, and B. K. Lee. 2007. Genetic diversity and population structure of *Liriope platyphylla* (Liliaceae) in Korea. J. Life Sci. 17, 328-333). In oriental medicine, *Liriope platyphylla* has been used as a therapeutic agent for treating ailments such as coughs, phlegm, and the like in Korean and China. In recent years, the plant has been known to be effective for treating diabetes, improving memory, inhibiting microbes, relieving inflammation, and the like.

"*Panax ginseng*" is a plant that grows in deep mountainous areas, grows to a height of 60 cm, and has a short rhizome standing upright or askew, and the root develops in the ground like a balloon flower. Generally, the plant is widely cultivated in Korea and China, and *Panax ginseng* is known to recover strength, treat physical weakness, weariness, fatigue, loss of appetite, vomiting, and diarrhea, enhance a pulmonary function, produce an essence and improve a resting effect and a renal function.

"*Cnidium officinale* Makino" is a perennial plant that belongs to the family Apiaceae, is native to China and is cultivated in regions such as China, Korea, Japan, and the like. The antioxidant activity (Lee et al., 2002) and the anti-platelet aggregation activity (Zhang L et al., 2009) are reported as the physiological actions of *Cnidium officinale* Makino.

"*Cyperi Rhizoma*" is a rhizome of *Cyperus rotundus* that is a perennial plant of the family Cyperaceae, and contains essential oils, alkaloids, flavonoids, sugars, pectin, and the like. A fluid extract of the rhizome of *Cyperi Rhizoma* is known to be effective for analgesia, relieving uterine tension, and improving a cardiotonic action, a micturition action and blood circulation. In oriental medicine, *Cyperi Rhizoma* has been widely used as a hemagogue and a hematocathartic agent to treat dysmenorrhea and pre- and post-partum women's disorders, and is added to an antipyretic/sedative medicine or a digestive medicine so that it is used to treat a cough, a headache, a stomachache, and the like. In connection with cosmetics, *Cyperi Rhizoma* is known to have a strong antibacterial effect on dermatophytes, promote blood circulation to have a healthy complexion, and be effective for preventing skin aging due to an antioxidant action and an anti-inflammatory action.

"*Morus Alba* bark" is a dry bark of roots of *Morus Alba* or plants belonging to the same genus as *Morus Alba*, and has been widely used as a cough suppressant, an anti-inflammatory agent, and a diuretic agent for oriental medicinal preparations in the past. The *Morus Alba* bark is known to have excellent analgesic, diuretic, cough-suppressant, anti-edema, sedative, anti-convulsant and hypotensive actions, and is often used as a traditional folk remedy disclosed in the Hyangyak Jipseongbang (i.e., Collection of Native Prescriptions to Save Life) in order to treat diseases associated with dandruff, itching and hair loss.

"*Perilla ocymoides*" is an annual plant that belongs to the family Lamiaceae, used after an entire plot of the plant is cut in late summer and dried in shade, and is disclosed in the Ben Cao Gang Mu (Compendium of Materia Medica) to have a spicy taste and a warm quality so that menopause, a nasal speculum, and a gastroscope are affected. It was found that *Perilla ocymoides* removes wind cold by producing sweat, allows energy to flow in the stomach, stabilizes a fetus, detoxifies fish poison, and has a weak antipyretic action, a stomachic action, an antibacterial action, a preservative action, and the like in a pharmacological experiment. Also, *Perilla ocymoides* is used to treat symptoms of wind cold, symptoms such as false and stiff senses of satiety caused by energy blockage in the stomach, vomiting and diarrhea symptoms, coughing and breathless symptoms caused by a cold-phlegm pattern/syndrome, and vomiting of a pregnant woman, fetal movement anxiety caused by gas, fish poisoning, and the like.

"*Portulaca oleracea*" is an annual grass that belongs to the genus *Portulaca* of the family Portulacaceae of the class Dicotyledoneae of the phylum Angiospermae of a purslane, and is referred to as 'Soebireum,' 'Oheangcho,' 'Jangmyeongchae,' 'Machichae,' and the like. *Portulaca oleracea* is known to have pharmacological effects such as an detoxification effect and effects on diuresis and dysentery, and is referred to as 'Mahyeon,' 'Oheangcho,' 'Gudusajacho,' 'Machichae,' "Machicho," 'Sanhyeon,' 'Andongchae,' 'Obangcho,' 'Jangmyeongchae,' 'ragweed,' 'Dodukpul,' 'Malbireum,' and the like.

"*Scutellaria baicalensis*" is a perennial plant that belongs to the family Lamiaceae, grows in meadows in mountainous areas, and grows to a height of 20 to 60 cm. In oriental medicine, the root of *Scutellaria baicalensis* is used as an antipyretic, a diuretic agent, an antidiarrheal agent, a choleretic agent, and an anti-inflammatory agent. Also, *Scutellaria baicalensis* contains baicalin that is one of flavonoids, and thus is known to have antioxidant, anticancer, anti-inflammatory effects.

"*Angelicae Gigantis* Radix" is a root of *Angelica gigas* Nakai that is a perennial plant that belongs to the family Apiaceae. Mountain and alpine regions of central and northern districts in Korea are known to be places suitable for cultivation thereof, and the root has been used as a medicinal and edible material for a long time. *Angelicae Gigantis* Radix is known to contain coumarins, essential oils, and polyacetylenes, and include decursin, decursinol angelate, and the like as main active ingredients. In oriental medicine, the root is known to have pharmacological effects such as an antibacterial effect, effects on fatigue recovery and blood nourishment and therapeutic effects on anemia and women's disorders.

"*Coptis chinensis*" is a perennial plant that belongs to the family Ranunculaceae. *Coptis chinensis* is known to contain alkaloid compounds such as berberine, coptisine, palmatine, and the like, and components such as obacunone, obaculactone, and the like. The effects of *Coptis chinensis* are known to include an antibacterial action, a hypotensive action, an action of smooth muscle relaxation in an organ such as a womb, and the like.

"*Flos Sophora japonica* Linne" is a flower and flower bud of a leguminous plant that belongs to *Styphnolobium japonicum* belonging to the family *Trifolium repens*, and classified as a high-quality product together with *Sophorae fructus* in the Shen Nong Ben Cao Jing (Divine Farmer's Classic of Materia Medica). In oriental medicine, *Flos Sophora japonica* Linne is known to have a bitter taste and a cold quality in a pharmacological aspect, reduce a fever and cool blood when it returns to the liver and large intestine, stop the bleeding, and treat nystagmus caused by ophthalmorrhagia, hypotension and cerebral apoplexy. Also, *Flos Sophora japonica* Linne is known to promote hair growth and growth and development of a healthy scalp because it has an activity of promoting the growth of dermal papilla cells and human keratinocytes.

"*Phellodendron amurensis*" is a bark of the Amur cork tree, which is also referred to as a *Phellodendron* bark. *Phellodendron amurensis* is distributed in the entire region other than the Jeju and Jeonnam regions in Korea, and also distributed in other regions such as Japan, Manchuria, China, Amur and Ussuri, and grows in thickets or mountain streams. The bark is peeled off from the stalk of *Phellodendron amurensis* to remove a rough bark or cut, and dried in the sun so that the bark is used as a medicine. In this regard, the bark is known to have a hypoglycemic action.

"*Polygonum Multiflorum*" is a perennial plant that belongs to the family Polygonaceae and is a medicinal climbing plant. The plant is used as a tonic agent, an energy booster, an emmenagogue, a hemostatic agent, and a cough suppressant, and is known to be used to treat colds, hematemesis, neurasthenia, and arthritis.

"*Houttuynia cordata* thunb." is an entire plant grass of *Heartleaf Houttuynia* that is a plant of the family Saururaceae, and grows in regions such as Southeast Asia and particularly in Japan, Korea, and the like. In a pharmacological aspect, the plant is known to have cardiotonic, diuretic, antibacterial, detoxification, and anticancer effects, and has been used in cosmetics and health functional foods which are helpful in detoxification and makeup among ordinary people. *Houttuynia cordata* thunb. is known to include large amounts of decanoyl acetaldehyde compounds, which have antibacterial, antiviral, and antimycotic effects, and flavonoid-based compounds, which have diuretic, cardiotonic, and cathartic effects.

The "extract" refers to an active ingredient included in a raw material extracted by allowing the extracted raw material to come into contact with a solvent. In this case, the extract may include all types of materials regardless of an extraction method or types of components as long as the extract is a material in which components included in the raw material are isolated from a natural substance.

For example, the extract may include all types of materials such as components dissolved in a solvent, which are extracted from a natural substance using water or an organic solvent, certain components (i.e., oils, and the like) obtained by extracting the natural substance, and the like. The extract is dried and ground into powder, or may be obtained by various extraction methods known in the art, such as a hot water extraction method, an ethanol extraction method, and the like.

The extracts may be extracted with one or more solvents selected from the group consisting of water, an anhydrous or hydrated lower alcohol having 1 to 4 carbon atoms, acetone, petroleum ether, ethyl acetate, butyl acetate, trichloromethane, dichloromethane, chloroform, hexane, and 1,3-butylene glycol. Specifically, the extract may be extracted with a 60 to 80% concentration (v/v) of ethanol.

An extraction ratio of the active ingredient included in the raw material may vary depending on the polarity of the solvent. Because the ethanol has excellent selectivity in extracting a physiologically active substance from a natural raw material, the optimum skin-improving effect may be realized through the ethanol extraction.

Because water and ethanol have different polarities and different active ingredients are extracted depending on the polarities of the water and ethanol, a concentration of the ethanol may be properly controlled to realize the optimum skin-improving effect. In this case, when the concentration of the ethanol is less than 60%, the active ingredient having a skin-improving effect may not be sufficiently extracted. On the other hand, when the concentration of the ethanol is greater than 80%, a proper yield may not be realized.

The extract may be prepared by washing the extracted raw material with water, drying the raw material, grinding the raw material into powder, extracting the ground raw material in a solvent whose volume is 8 to 12 times higher than the weight of the raw material for approximately 1 to 24 hours using conventional methods such as reflux circulation extraction, pressing extraction, ultrasonic extraction, and the like, and filtering the extracted raw material. Also, the extract may be obtained in a powdery phase using an additional process such as vacuum distillation or freeze drying.

The extract may also include an extract subjected to a conventional purification process. For example, the extract may include fractions obtained through various purification methods additionally performed, such as separation using an ultrafiltration membrane having a constant molecular weight cut-off value, separation using various types of chromatography (manufactured for separation based on size, charge, hydrophobicity or hydrophilicity), and the like.

The extract may be extracted at a temperature of 50° C. to 90° C. for 12 to 18 hours using ethanol as the solvent.

Meanwhile, when the extraction temperature is less than 50° C., extraction efficiency may be degraded, and the active ingredient may not be suitably eluted. On the other hand, when the extraction temperature is greater than 90° C., the active ingredient included in the natural raw material may be modified or lost at a high temperature, resulting in a reduced skin-improving effect. Therefore, it is desirable that the extraction temperature is maintained within this temperature range. Also, when the extraction time is less than 12 hours, the active ingredient included in the natural raw material may not be completely extracted. On the other hand, when the extraction time is greater than 18 hours, the residual active ingredient included in the natural raw material is excessively high, resulting in inefficiency in terms of time and cost. Therefore, it is desirable that the extraction time is properly controlled.

The cosmetic composition may be used for antioxidant and whitening purposes.

The term "antioxidative" refers to an action to inhibit oxidation. A human body keeps a balance between prooxidants and antioxidants, but, when such a balance is lost due to various factors and tilted toward promoting oxidation, oxidative stress is induced in vivo to cause cell damage and pathological diseases.

Because reactive oxygen species (ROS) directly causing the oxidative stress are chemically unstable and highly reactive, the ROS may easily react with various biomaterials such as DNA, proteins, lipids, and carbohydrates, and may also attack in vivo polymers to cause irreversible damage to cells and tissues or produce mutations, cytotoxicity and cancer, and may directly cause aging. When an antioxidant effect is achieved by removing or reducing the ROS, aging may be prevented and a healthy condition may be maintained.

The term "whitening" refers to an effect of relieving skin pigmentation phenomena such as blemishes, freckles, spots, and the like by suppressing generation of various biomolecules such as melanin, redox haemoglobin, carotenes, melanoids, and the like, all of which have an influence on skin tone, and improving skin brightness and uniformity by reducing the yellowness and redness of the skin.

The cosmetic composition may be formulated into one or more selected from the group consisting of an emulsifying toner, a nourishing toner, a moisturizing cream, a nourishing cream, a massage cream, a nourishing lotion, an essence, an ampoule, a gel, an eye cream, an oil, a foundation, a cleansing cream, a cleansing foam, a cleansing water, a shampoo, a rinse, a pack, a spray, and a powder.

The cosmetic composition may be formulated using a conventional method. For formulation of liquids for external use for the skin, see the contents disclosed in Remington's Pharmaceutical Science, Mack Publishing Company, Easton Pa. For formulation of the cosmetic composition, see the contents disclosed in the International Cosmetic Ingredient Dictionary, 6th ed (The Cosmetic, Toiletry and Fragrance Association, Inc., Washington, 1995).

Specifically, the cosmetic composition may be prepared into typical emulsion formulations and solubilized formulations. For example, the cosmetic composition may be formulated into toners such as an emulsifying toner or a nourishing toner; lotions such as a facial lotion, a body lotion, and the like; creams such as a nourishing cream, a moisturizing cream, an eye cream, and the like; essences; cosmetic balms; sprays; gels; packs; sunscreens; makeup bases; liquid-, solid- or spray-type foundations; powders; makeup removers such as a cleansing cream, a cleansing lotion, a cleansing oil, and the like; or detergents such as cleansing foam, soap, a body wash, and the like, but the present invention is not limited thereto. Also, the liquids for external use for the skin may be formulated into ointments, patches, gels, creams, or sprays, but the present invention is not limited thereto.

In the cosmetic composition, in addition to the essential components in each formulation, other components may be properly blended in a range which does not hinder an object of the present invention, depending on the type of the formulation and the purpose of use.

The cosmetic composition may include a typically available carrier. For example, an oil, water, a surfactant, a moisturizing agent, a lower alcohol, a thickening agent, a chelating agent, a pigment, a preservative, a fragrance and the like may be properly blended, but the present invention is not limited thereto.

Types of the available carrier may vary depending on the formulation. For example, when the composition is formulated into ointments, pastes, creams or gels, an animal oil, a vegetable oil, wax, paraffin, starch, tragacanth, a cellulose derivative, polyethylene glycol, silicon, bentonite, silica, talc, zinc oxide, or a mixture thereof may be used as the carrier component.

When the cosmetic composition is formulated into powders or sprays, lactose, talc, silica, aluminum hydroxide, calcium silicate, polyamide powder, or a mixture thereof may be used as the carrier component. In the case of sprays, the cosmetic composition may further include a propellant such as chlorofluorohydrocarbon, propane, butane, or dimethyl ether.

When the cosmetic composition is formulated into solutions or emulsions, a solvent, a solubilizing agent, or an emulsifying agent may be used as the carrier component. For example, water, ethanol, isopropanol, ethyl carbonate, ethyl acetate, benzyl benzoate, propylene glycol, 1,3-butyl glycol oil may be used. In particular, cottonseed oil, peanut oil, corn seed oil, olive oil, castor oil and sesame oil, a glycol fatty acid ester, polyethylene glycol, or a fatty acid ester of sorbitan may be used.

When the cosmetic composition is formulated into suspensions, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, or tragacanth may be used as the carrier component.

When the cosmetic composition is formulated into soap, an alkali metal salt of a fatty acid, a fatty acid hemi-ester salt, fatty acid protein hydrolysate, an isethionate, a lanolin derivative, a fatty alcohol, a vegetable oil, glycerol, a sugar, and the like may be used as the carrier component.

The cosmetic composition may further include adjuvants typically used in the field of cosmetics or dermatology, such as lipids typically used in the related art, an organic solvent, a dissolving agent, a concentrating agent, a gelling agent, a softening agent, an antioxidant, a suspending agent, a stabilizing agent, a foaming agent, a flavoring agent, a surfactant, water, an ionic or non-ionic emulsifying agent, a filler, a metal ion sequestering agent, a chelating agent, a preservative, a blocking agent, a moisturizing agent, an essential oil, a dye, a pigment, a hydrophilic or lyphophilic active agent, and other components typically used in cosmetics, depending on the quality and function of the final products.

However, the adjuvants and mixing ratios thereof may be properly chosen so that the adjuvants have no influence on the desirable properties of the cosmetic composition according to the present invention.

Hereinafter, the present invention will be described in further detail with reference to embodiments thereof. However, it will be apparent that the following embodiments are not intended to limit the scope of the present invention.

PREPARATION EXAMPLE

Preparation of Natural Extract

*O. asiaticus*, *C. apiifolia*, *Magnolia officinalis*, *Blettia rhizome*, *Rhus semialata*, *Eleutherococcus senticosus* (Rupr. & Maxim.) Maxim. root, *Cyperi Rhizoma*, *Morus Alba* bark, *Perilla ocymoides*, *Portulaca oleracea*, *Phellodendron amurensis* and *Polygonum Multiflorum* were washed with water, completely dried at room temperature, and ground to obtain 100 g of ground products. 100 g of each of the ground products was immersed in a 20× volume of 80% ethanol used as a solvent, and extracted at room temperature for 7 days.

The extracts were filtered through a 3 μm filter with 250 mesh, concentrated at 40° C. under reduced pressure, and then freeze-dried to obtain solid extracts.

EXAMPLES AND COMPARATIVE EXAMPLES

To verify a skin-improving effect of the samples thus prepared, the samples were mixed as listed in the following Tables 1 and 2 to configure Examples and Comparative Examples.

TABLE 1

[Content (part(s) by weight)]

| Items | Examples | | | | | | | | |
|---|---|---|---|---|---|---|---|---|---|
| | 1 | 2 | 3 | 4 | 5 | 6 | 7 | 8 | 9 |
| *O. asiaticus* extract | 30 | 25 | 25 | 25 | 25 | 25 | 25 | 25 | 25 |
| *C. apiifolia* extract | 30 | 25 | 25 | 25 | 25 | 25 | 25 | 25 | 25 |
| *Magnolia officinalis* extract | — | 5 | — | — | — | — | 2 | — | 1 |
| *Blettia rhizome* extract | — | 5 | — | — | — | — | 2 | — | 1 |
| *Rhus semialata* extract | — | — | 5 | — | — | — | 2 | — | 1 |
| *Eleutherococcus senticosus* (Rupr. & Maxim.) Maxim. root extract | — | — | 5 | — | — | — | 2 | — | 1 |
| *Cyperi Rhizoma* extract | — | — | — | 5 | — | — | 2 | — | 1 |
| *Morus Alba* bark extract | — | — | — | 5 | — | — | 2 | — | 1 |
| *Perilla ocymoides* extract | — | — | — | — | 5 | — | 2 | — | 1 |
| *Portulaca oleracea* extract | — | — | — | — | 5 | — | 2 | — | 1 |
| *Phellodendron amurensis* extract | — | — | — | — | — | 5 | 2 | — | 1 |
| *Polygonum Multiflorum* extract | — | — | — | — | — | 5 | 2 | — | 1 |

TABLE 2

[Content (part(s) by weight)]

| Items | Comparative Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| *O. asiaticus* extract | 60 | — | — | — | — | — | — | — | — | — | — | — |
| *C. apiifolia* extract | — | 60 | — | — | — | — | — | — | — | — | — | — |
| *Magnolia officinalis* extract | — | — | 60 | — | — | — | — | — | — | — | — | — |
| *Blettia rhizome* extract | — | — | — | 60 | — | — | — | — | — | — | — | — |
| *Rhus semialata* extract | — | — | — | — | 60 | — | — | — | — | — | — | — |
| *Eleutherococcus senticosus* (Rupr. &Maxim.) Maxim. Root extract | — | — | — | — | — | 60 | — | — | — | — | — | — |
| *Cyperi Rhizoma* extract | — | — | — | — | — | — | 60 | — | — | — | — | — |
| *Morus Alba* bark extract | — | — | — | — | — | — | — | 60 | — | — | — | — |
| *Perilla ocymoides* extract | — | — | — | — | — | — | — | — | 60 | — | — | — |
| *Portulaca oleracea* extract | — | — | — | — | — | — | — | — | — | 60 | — | — |
| *Phellodendron amurensis* extract | — | — | — | — | — | — | — | — | — | — | 60 | — |
| *Polygonum Multiflorum* extract | — | — | — | — | — | — | — | — | — | — | — | 60 |

Experimental Example 1

Skin Safety Test

To verify the safety of the samples of Examples and Comparative Examples with respect to skin, an MTT assay was performed on fibroblasts (HDF), melanocytes (B16F10), and keratinocytes (HaCaT).

Each of the samples of Examples and Comparative Examples was suspended in purified water at an increasing concentration of 0, 1, 5, 10, 20, 50, and 100 mg/L, and cell survival rates were measured.

Cytotoxicity was determined using a modified Mosmann's method in which the cell survival rates were measured using a 3-(4,5-dimethylthiazol-2-yl)-2-5-diphenyltetrazolium bromide (MTT) reagent.

Each of the fibroblasts (HDF), melanocytes (B16F10), and keratinocytes (HaCaT) were seeded at a concentration of $1 \times 10^4$ cells/well in a 96-well plate, and cultured at 37° C. and 5% $CO_2$ for 48 hours.

After the culture medium was removed, the cells were cultured for 48 hours in a medium treated with a varying concentration of each of the samples, and the medium was removed. Thereafter, the cultured cells were repeatedly washed with phosphate buffered saline (PBS).

MTT was dissolved at a concentration of 5 mg/mL in PBS, and 50 μL of the MTT solution was added to the cells. Then, the cells were cultured at 37° C. and 5% $CO_2$ for 48 hours. Dimethyl sulfoxide (DMSO) was added at an amount of 100 L/well, and stirred for 10 minutes. Then, the optical density at 540 nm was measured.

The results of measurement showed that the samples exhibited no cytotoxicity at all the concentrations thereof. The results suggested that the samples were not harmful to the human body and had excellent safety with respect to the human body.

Experimental Example 2

Evaluation of Free Radical Scavenging Activity by DPPH Assay

Each of the extracts of Examples and Comparative Examples was suspended in purified water to evaluate a free radical scavenging activity of each of the extracts.

A DPPH assay is a method of measuring an optical density at 540 nm to measure a level of discoloration caused by an inhibitor scavenging stable 2,2-diphenyl-1-picrylhydrazyl (DPPH) radicals.

Vitamin C was used as the control, and a 50% scavenging concentration ($SC_{50}$) of the DPPH radicals was measured. Then, the measured $SC_{50}$ of the DPPH radicals was compared to that of the control (Table 3).

Figure 1:
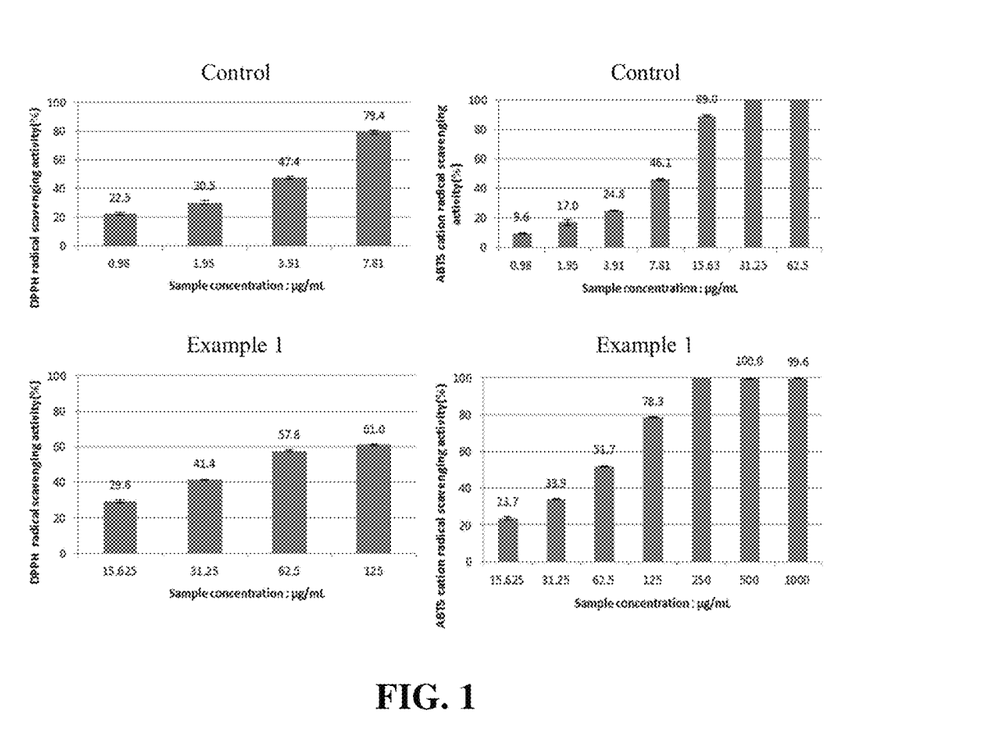
FIG. 1 is a graph illustrating results of comparing antioxidant capacity of a composition prepared according to one exemplary embodiment of the present invention with the control.
Figure 2:
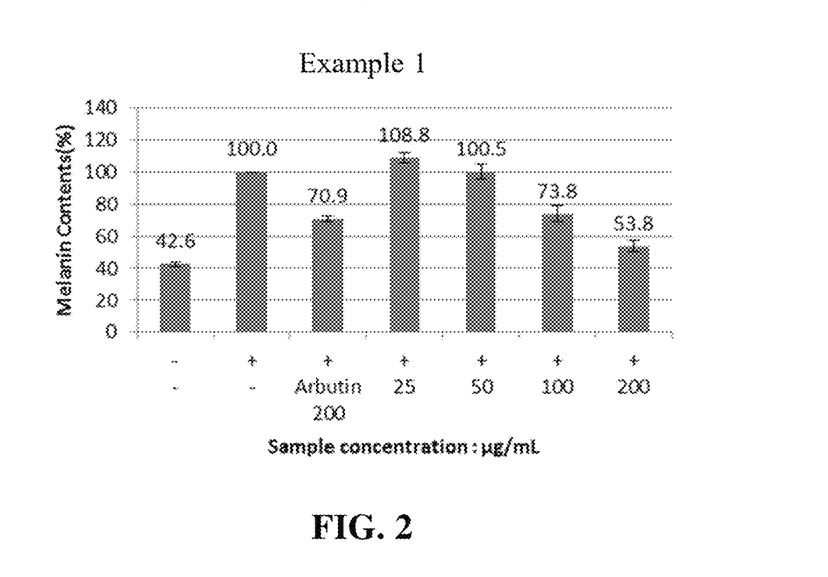
FIG. 2 is a graph illustrating a whitening effect of the composition prepared according to one exemplary embodiment of the present invention.

In particular, the free radical scavenging activity of the sample of Example 1 at different concentrations was measured, and compared to that of the control (FIG. 1).

TABLE 3

[50% Scavenging Concentration ($SC_{50}$) of DPPH Radicals]

| Items | $SC_{50}$ (μg/mL) |
|---|---|
| Example 1 | 48.4 |
| Example 2 | 41.2 |
| Example 3 | 42.1 |
| Example 4 | 43.1 |
| Example 5 | 42.5 |
| Example 6 | 42.6 |
| Example 7 | 38.2 |
| Example 8 | 39.9 |
| Example 9 | 35.6 |
| Comparative Example 1 | 53.2 |
| Comparative Example 2 | 54.6 |
| Comparative Example 3 | 85.3 |
| Comparative Example 4 | 82.8 |
| Comparative Example 5 | 83.3 |
| Comparative Example 6 | 77.4 |
| Comparative Example 7 | 83.2 |
| Comparative Example 8 | 77.5 |
| Comparative Example 9 | 75.3 |
| Comparative Example 10 | 72.1 |
| Comparative Example 11 | 82.4 |
| Comparative Example 12 | 84.6 |
| Control (Vitamin C) | 8.7 |

Referring to Table 3, a lower value of $SC_{50}$ indicates a higher DPPH free radical scavenging activity.

It was estimated that the higher the free radical scavenging activity was, the superior the antioxidant effect was. The samples of Examples 1 to 9 including the *O. asiaticus* extract and the *C. apiifolia* extract had a significantly superior free radical scavenging activity, compared to the samples of Comparative Examples 1 to 12 including the single extract.

In particular, the sample of Example 1 including both the *O. asiaticus* and the *C. apiifolia* extract had a significantly improved free radical scavenging activity, compared to the samples of Comparative Examples 1 and 2 including either the *O. asiaticus* or *C. apiifolia* extract. The results suggested that a combination of the *O. asiaticus* extract and the *C. apiifolia* extract remarkably improved the antioxidant activity.

Also, the samples of Examples 2 to 9 including the *O. asiaticus* and *C. apiifolia* extracts and one or more selected from *Magnolia officinalis*, *Blettia rhizome*, *Rhus semialata*, *Eleutherococcus senticosus* (Rupr. & Maxim.) Maxim. root, *Cyperi Rhizoma*, *Morus Alba* bark, *Perilla ocymoides*, *Portulaca oleracea*, *Phellodendron amurensis*, and *Polygonum Multiflorum* extracts had a further improved antioxidant activity, compared to the sample of Example 1.

Experimental Example 3

Evaluation of Free Radical Scavenging Activity by ABTS Assay

Each of the extracts of Examples and Comparative Examples was suspended in purified water to evaluate a free radical scavenging activity of each of the extracts.

An ABTS assay is a method of measuring a level of conversion of bluish green 2,2'-azino-di(3-ethylbenzthiazoline-6-sulfonic acid) radicals into colorless ABTS at 732 nm caused by an antioxidant scavenging the bluish green ABTS radicals.

Vitamin C was used as the control, and a 50% scavenging concentration ($SC_{50}$) of the ABTS radicals was measured. Then, the measured $SC_{50}$ of the ABTS radicals was compared to that of the control (Table 4).

In particular, the free radical scavenging activities at different concentrations were measured in the case of Example 1, and compared to that of the control (FIG. 1).

TABLE 4

[50% Scavenging Concentration (SC$_{50}$) of ABTS Radicals]

| Items | SC$_{50}$ (μg/mL) |
| --- | --- |
| Example 1 | 59.3 |
| Example 2 | 51.2 |
| Example 3 | 52.1 |
| Example 4 | 53.1 |
| Example 5 | 52.5 |
| Example 6 | 52.6 |
| Example 7 | 52.4 |
| Example 8 | 52.3 |
| Example 9 | 45.6 |
| Comparative Example 1 | 78.4 |
| Comparative Example 2 | 66.6 |
| Comparative Example 3 | 81.2 |
| Comparative Example 4 | 88.1 |
| Comparative Example 5 | 84.4 |
| Comparative Example 6 | 82.9 |
| Comparative Example 7 | 84.3 |
| Comparative Example 8 | 98.1 |
| Comparative Example 9 | 83.5 |
| Comparative Example 10 | 81.3 |
| Comparative Example 11 | 95.8 |
| Comparative Example 12 | 83.7 |
| Control (Vitamin C) | 8.7 |

Referring to Table 4, a lower value of SC$_{50}$ indicates a higher free radical scavenging activity.

It was estimated that the higher the free radical scavenging activity was, the superior the antioxidant effect was. The samples of Examples 1 to 9 including the *O. asiaticus* extract and the *C. apiifolia* extract had a significantly superior free radical scavenging activity, compared to the samples of Comparative Examples 1 to 12 including the single extract.

In particular, the sample of Example 1 including both the *O. asiaticus* and the *C. apiifolia* extract had a significantly improved free radical scavenging activity, compared to the samples of Comparative Examples 1 and 2 including either the *O. asiaticus* or *C. apiifolia* extract. The results suggested that a combination of the *O. asiaticus* extract and the *C. apiifolia* extract remarkably improved the antioxidant activity.

Also, the samples of Examples 2 to 9 including the *O. asiaticus* and *C. apiifolia* extracts and one or more selected from *Magnolia officinalis*, *Blettia rhizome*, *Rhus semialata*, *Eleutherococcus senticosus* (Rupr. & Maxim.) Maxim. root, *Cyperi Rhizoma*, *Morus Alba* bark, *Perilla ocymoides*, *Portulaca oleracea*, *Phellodendron amurensis*, and *Polygonum Multiflorum* extracts had a further improved antioxidant activity, compared to the sample of Example 1.

Experimental Example 4

Measurement of Total Content of Polyphenol-based Compounds

To measure the total amount of polyphenol-based compounds included in the samples of Examples and Comparative Examples, colorimetric quantification was carried out according to the Folin-Denis method.

5 mL of distilled water was added to 100 μL of each of the extracts of Examples and Comparative Examples, and 1 mL of a folin reagent was added thereto. Thereafter, 1.5 mL of a 20% Na$_2$CO$_3$ solution was added thereto, and mixed. The resulting mixture was kept at room temperature for 2 hours, and an optical density of the mixture at 765 nm was measured.

The total polyphenol content was expressed as a gallic acid equivalent (GAE), and the polyphenols included in each of the extracts were quantified using a pre-constructed standard curve for gallic acid.

TABLE 5

| Items | Total content of polyphenol compounds (μg GAE/1 mg) |
| --- | --- |
| Example 1 | 90.6 |
| Example 2 | 84.1 |
| Example 3 | 81.8 |
| Example 4 | 85.3 |
| Example 5 | 83.4 |
| Example 6 | 84.6 |
| Example 7 | 99.1 |
| Example 8 | 98.8 |
| Example 9 | 92.4 |
| Comparative Example 1 | 90.4 |
| Comparative Example 2 | 83.2 |
| Comparative Example 3 | 82.8 |
| Comparative Example 4 | 78.1 |
| Comparative Example 5 | 81.5 |
| Comparative Example 6 | 78.4 |
| Comparative Example 7 | 81.8 |
| Comparative Example 8 | 84.4 |
| Comparative Example 9 | 78.9 |
| Comparative Example 10 | 76.1 |
| Comparative Example 11 | 77.5 |
| Comparative Example 12 | 75.7 |

Because the polyphenols were antioxidants having an antioxidant effect, it was estimated that the higher the total content of the polyphenol in each of the extracts was, the superior the antioxidant effect was.

Experimental Example 5

Determination of Amount of Produced Melanin

To check a whitening effect of the samples of Examples and Comparative Examples, an ability of the samples of Examples and Comparative Examples to inhibit melanogenesis was evaluated using a melanin content assay (Eisinger M et al., 1982; Siegrist W and Eberle A N, 1986). Each of the samples of Examples and Comparative Examples was suspended at a concentration of 50 mg/L in purified water, and an amount of produced melanin was determined.

B16F10 cells were seeded at a concentration of 1.5×10$^5$ cells/well in a 60 mm culture dish, and then cultured for 24 hours. A melanogenesis-stimulating hormone, α-MSH (Sigma-Aldrich, St. Louis, Mo., USA), and each of the samples of Examples and Comparative Examples were added to a medium at a concentration of 200 μg/mL (Virador V M et al., 1999).

After 48 hours had elapsed, the cells were harvested, and then washed once with PBS. Thereafter, 120 μL of a 1 N NaOH lysis buffer was added thereto, and the resulting mixture was heated at 95° C. for 10 minutes to lyse the cells. The optical density at a wavelength of 450 nm was measured using a microplate reader. Here, arbutin at a concentration of 200 μg/mL was used as the control (Table 6).

In particular, the melanin production rates at different concentrations were measured in the case of Example 1 (FIG. 1).

TABLE 6

| Items | Melanin production rate (%) |
|---|---|
| Example 1 | 53.8 |
| Example 2 | 51.1 |
| Example 3 | 52.2 |
| Example 4 | 52.3 |
| Example 5 | 53.1 |
| Example 6 | 53.1 |
| Example 7 | 49.7 |
| Example 8 | 47.2 |
| Example 9 | 45.1 |
| Comparative Example 1 | 52.1 |
| Comparative Example 2 | 68.6 |
| Comparative Example 3 | 74.4 |
| Comparative Example 4 | 84.1 |
| Comparative Example 5 | 82.4 |
| Comparative Example 6 | 81.9 |
| Comparative Example 7 | 75.1 |
| Comparative Example 8 | 83.4 |
| Comparative Example 9 | 77.9 |
| Comparative Example 10 | 76.7 |
| Comparative Example 11 | 81.2 |
| Comparative Example 12 | 74.1 |
| Positive control | 38.2 |

It was estimated that the more the melanogenesis was inhibited, the superior the whitening effect was. The samples of Examples 1 to 9 including the *O. asiaticus* extract and the *C. apiifolia* extract inhibited melanogenesis at a higher level, compared to the samples of Comparative Examples 1 to 12 including the single extract.

In particular, the sample of Example 1 including both the *O. asiaticus* and the *C. apiifolia* extract had a significantly improved inhibitory effect on melanogenesis, compared to the samples of Comparative Examples 1 and 2 including either the *O. asiaticus* or *C. apiifolia* extract, indicating that a combination of the *O. asiaticus* extract and the *C. apiifolia* extract remarkably improved the whitening effect.

Also, the samples of Examples 2 to 9 including the *O. asiaticus* and *C. apiifolia* extracts and one or more selected from *Magnolia officinalis*, *Blettia rhizome*, *Rhus semialata*, *Eleutherococcus senticosus* (Rupr. & Maxim.) Maxim. root, *Cyperi Rhizoma*, *Morus Alba* bark, *Perilla ocymoides*, *Portulaca oleracea*, *Phellodendron amurensis*, and *Polygonum Multiflorum* extracts had a further improved whitening effect, compared to the sample of Example 1.

Experimental Example 6

Evaluation of Skin Tone-improving Effect

A skin tone-improving effect of the cosmetic composition including each of the samples obtained in Examples and Comparative Examples was evaluated. The samples of Examples and Comparative Examples were formulated into creams having the same compositions. In this case, only the samples of Examples and Comparative Examples differed.

Creams into which the samples of Examples and Comparative Examples were formulated were applied to 210 women selected with an age group ranging from 20 to 60 years old to evaluate a degree of skin tone improvement.

The 210 women were divided into 21 groups of tens, and instructed to apply the formulated creams onto their whole faces twice a day for 12 weeks under conditions of a temperature of 24 to 26° C. and a humidity of 75%. Thereafter, the skin tone-improving effects were evaluated through visual evaluation by experts.

TABLE 7

| Items | Significantly improved (No.) | Slightly improved (No.) | Not improved (No.) |
|---|---|---|---|
| Example 1 | 3 | 2 | 5 |
| Example 2 | 6 | 3 | 1 |
| Example 3 | 4 | 2 | 4 |
| Example 4 | 4 | 2 | 4 |
| Example 5 | 5 | 3 | 2 |
| Example 6 | 4 | 2 | 4 |
| Example 7 | 5 | 2 | 3 |
| Example 8 | 4 | 3 | 3 |
| Example 9 | 7 | 2 | 1 |
| Comparative Example 1 | 1 | 1 | 8 |
| Comparative Example 2 | 2 | 1 | 7 |
| Comparative Example 3 | 2 | 2 | 6 |
| Comparative Example 4 | 2 | 1 | 7 |
| Comparative Example 5 | 3 | 1 | 6 |
| Comparative Example 6 | 2 | 1 | 7 |
| Comparative Example 7 | 2 | 2 | 6 |
| Comparative Example 8 | 1 | 2 | 7 |
| Comparative Example 9 | 2 | 2 | 6 |
| Comparative Example 10 | 3 | 1 | 6 |
| Comparative Example 11 | 2 | 1 | 7 |
| Comparative Example 12 | 2 | 2 | 6 |

Referring to Table 7, it was estimated that the samples of Examples 1 to 9 including the *O. asiaticus* extract and the *C. apiifolia* extract had a significantly superior skin tone-improving effect, compared to the samples of Comparative Examples 1 to 12 including the single extract.

In particular, the sample of Example 1 including both the *O. asiaticus* and the *C. apiifolia* extract had a significantly improved skin tone-improving effect, compared to the samples of Comparative Examples 1 and 2 including either the *O. asiaticus* or *C. apiifolia* extract.

Experimental Example 7

Evaluation of Skin Elasticity-improving Effect

A skin elasticity-improving effect of the cosmetic composition including each of the samples obtained in Examples and Comparative Examples was evaluated. The respective samples were formulated into creams having the same compositions. In this case, only the samples of Examples 1 to 9 and Comparative Examples 1 to 12 differed.

Healthy women over the age of 20 years old (with an average age of 37 years old) were divided into groups, and instructed to apply the formulated creams of Examples and Comparative Examples onto their faces under conditions of a temperature of 24 to 26° C. and a humidity of 75%.

The formulated creams were applied around the eyes twice (morning and evening) a day for 12 weeks, and the skin elasticity was measured using a skin elastometer (Cutometer MPA580 commercially available from Courage+ Khazaka Electronic GmbH, Germany). The test results were expressed as R8 (R8 (week 12)–R8 (week 0)) values of the Cutometer MPA580, and the R8 values represented properties such as skin viscoelasticity. The results are listed in the following Table 8.

TABLE 8

| Items | Skin elasticity-improving effect |
|---|---|
| Example 1 | 0.65 |
| Example 2 | 0.77 |
| Example 3 | 0.72 |
| Example 4 | 0.73 |

TABLE 8-continued

| Items | Skin elasticity-improving effect |
| --- | --- |
| Example 5 | 0.72 |
| Example 6 | 0.71 |
| Example 7 | 0.73 |
| Example 8 | 0.72 |
| Example 9 | 0.78 |
| Comparative Example 1 | 0.42 |
| Comparative Example 2 | 0.44 |
| Comparative Example 3 | 0.42 |
| Comparative Example 4 | 0.34 |
| Comparative Example 5 | 0.34 |
| Comparative Example 6 | 0.34 |
| Comparative Example 7 | 0.35 |
| Comparative Example 8 | 0.32 |
| Comparative Example 9 | 0.35 |
| Comparative Example 10 | 0.34 |
| Comparative Example 11 | 0.34 |
| Comparative Example 12 | 0.25 |
| Positive control(vitamin C) | 0.92 |
| Negative control (untreated) | 0.31 |

The samples of Examples 1 to 9 including the *O. asiaticus* extract and the *C. apiifolia* extract had a significantly excellent skin elasticity-improving effect, compared to the samples of Comparative Examples 1 to 12 including the single extract.

In particular, the sample of Example 1 including both the *O. asiaticus* and the *C. apiifolia* extract had a significantly improved skin elasticity-improving effect, compared to the samples of Comparative Examples 1 and 2 including either the *O. asiaticus* or *C. apiifolia* extract.

Also, the samples of Examples 2 to 9 including the *O. asiaticus* and *C. apiifolia* extracts and one or more selected from *Magnolia officinalis, Blettia rhizome, Rhus semialata, Eleutherococcus senticosus* (Rupr. & Maxim.) Maxim. root, *Cyperi Rhizoma, Morus Alba* bark, *Perilla ocymoides, Portulaca oleracea, Phellodendron amurensis*, and *Polygonum Multiflorum* extracts had a further improved effect of enhancing skin elasticity, compared to the sample of Example 1.

The cosmetic composition according to one exemplary embodiment of the present invention has an excellent antioxidant and whitening effect because the cosmetic composition includes the *O. asiaticus* extract and the *C. apiifolia* extract.

In particular, the cosmetic composition has an excellent antioxidant effect because a content of a polyphenol-base compound as an antioxidant increases as the *O. asiaticus* extract and the *C. apiifolia* extract are fermented.

It should be understood that the effects of the present invention are not limited to the above-described effects, and encompasses all types of effects deducible from the configurations of the present invention disclosed in the detailed description and claims of the present invention.

It should be understood by those skilled in the art to which the present invention pertains that the description proposed herein is given for the purpose of illustration only, and various changes and modifications can be made to the above-described exemplary embodiments of the present invention without departing from the scope of the invention. Accordingly, the exemplary embodiments of the present invention are not intended to limit the scope of the invention but to describe the invention. For example, individual components described in an integral form may be implemented in a dispersed form, and individual components described in a dispersed form may also be implemented in an integral form.

The scope of the present invention is defined by the appended claims, and encompasses all modifications and alterations derived from meanings, the scope and equivalents of the appended claims.

What is claimed is:

1. An antioxidant and whitening cosmetic composition comprising an *Osmanthus asiaticus* (*O. asiaticus*) extract at 25 parts by weight, a *Clematis apiifolia* (*C. apiifolia*) extract at 25 parts by weight, a *Rhus semialata* extract at 5 parts by weight, and an *Eleutherococcus senticosus* (Rupr. & Maxim.) Maxim. root extract at 5 parts by weight as an active ingredient.

2. The cosmetic composition of claim 1, further comprising one or more selected from the group consisting of a *Puerariae radix* extract, a *Glycyrrhiza uralensis Fischer* extract, a *Farfarae flos* extract, a *Sophora flavescens* extract, a *Magnolia officinalis* extract, a *Blettia rhizome* extract, a *Persiccae Semen* extract, a *Liriope platyphylla* extract, a *Panax ginseng* extract, a *Cnidium officinale* Makino extract, a *Cyperi Rhizoma* extract, a *Morus Alba* bark extract, a *Perilla ocymoides* extract, a *Portulaca oleracea* extract, a *Scutellaria baicalensis* extract, an *Angelicae Gigantis* Radix extract, a *Coptis chinensis* extract, a *Flos Sophora japonica* Linne extract, a *Phellodendron amurensis* extract, a *Polygonum Multiflorum* extract, and a *Houttuynia cordata* thunb. extract.

3. The cosmetic composition of claim 1, wherein the extracts are extracted with one or more solvents selected from the group consisting of water, an anhydrous or hydrated lower alcohol having 1 to 4 carbon atoms, acetone, ether, ethyl acetate, butyl acetate, trichloromethane, dichloromethane, chloroform, hexane, and 1,3-butylene glycol.

4. The cosmetic composition of claim 2, wherein the extracts are extracted with one or more solvents selected from the group consisting of water, an anhydrous or hydrated lower alcohol having 1 to 4 carbon atoms, acetone, ether, ethyl acetate, butyl acetate, trichloromethane, dichloromethane, chloroform, hexane, and 1,3-butylene glycol.

5. The cosmetic composition of claim 1, wherein the cosmetic composition is formulated into one or more selected from the group consisting of an emulsifying toner, a nourishing toner, a moisturizing cream, a nourishing cream, a massage cream, a nourishing lotion, an essence, an ampoule, a gel, an eye cream, an oil, a foundation, a cleansing cream, a cleansing foam, a cleansing water, a shampoo, a rinse, a pack, a spray, and a powder.

6. The cosmetic composition of claim 2, wherein the cosmetic composition is formulated into one or more selected from the group consisting of an emulsifying toner, a nourishing toner, a moisturizing cream, a nourishing cream, a massage cream, a nourishing lotion, an essence, an ampoule, a gel, an eye cream, an oil, a foundation, a cleansing cream, a cleansing foam, a cleansing water, a shampoo, a rinse, a pack, a spray, and a powder.

* * * * *